United States Patent [19]

Niezink et al.

[11] Patent Number: 5,300,079

[45] Date of Patent: Apr. 5, 1994

[54] INJECTOR

[75] Inventors: Herman Niezink, Wierden; Jeroen J. M. Bolscher, Ootmarsum, both of Netherlands

[73] Assignee: Texas Instruments Incorporated, Dallas, Tex.

[21] Appl. No.: 90,555

[22] Filed: Jul. 12, 1993

Related U.S. Application Data

[63] Continuation of Ser. No. 827,133, Jan. 28, 1992, abandoned.

[30] Foreign Application Priority Data

Jan. 30, 1991 [NL] Netherlands .......................... 9100160

[51] Int. Cl.⁵ ............................................. A61M 36/12
[52] U.S. Cl. ..................................... 606/117; 604/60; 604/61; 604/116
[58] Field of Search ................... 606/116, 117; 604/57, 604/59-64, 112, 115-117

[56] References Cited

U.S. PATENT DOCUMENTS

| | | | |
|---|---|---|---|
| 2,198,666 | 4/1940 | Gruskin | 604/117 |
| 2,743,723 | 5/1956 | Hein | 604/115 |
| 2,859,749 | 11/1958 | Johnson | 604/157 |
| 4,114,619 | 9/1978 | Wagner | 604/115 |
| 4,403,610 | 9/1983 | Lodge et al. | 604/61 |
| 4,762,515 | 8/1988 | Grimm | 604/61 |

FOREIGN PATENT DOCUMENTS

| | | | |
|---|---|---|---|
| 364044 | 4/1990 | European Pat. Off. | 606/117 |
| 2612401 | 9/1988 | France | 604/117 |
| 8701027 | 11/1988 | Netherlands | 606/117 |
| 2138298A | 10/1984 | United Kingdom . | |

Primary Examiner—Ralph Lewis
Attorney, Agent, or Firm—Rebecca A. Mapstone; James C. Kesterson; Richard L. Donaldson

[57] ABSTRACT

Injector for inserting objects such as transponders (4) into a living being. The injector is provided with positioning means for fixing the position of the insertion needle (9) relative to the living being. These positioning means comprise a pin (5) designed to rest with the shank thereof against a part of the living being, such as the head (1). The position of the insertion needle (9) can thereby be determined irrespective of differences occurring from one animal to another.

12 Claims, 3 Drawing Sheets

INJECTOR

This application is a continuation of application Ser. No. 07/827,133 filed Jan. 28, 1992, now abandoned.

FIELD OF THE INVENTION

The present invention relates to an injector, comprising a grip, a hollow needle, means for conveying and placing objects via said needle in a body, and positioning means for fixing the position of the needle relative to said body, said positioning means comprising a pin-shaped member, fitted essentially parallel to the needle, which pin-shaped member is connected to the injector at one side.

BACKGROUND OF THE INVENTION

Such an injector is known from existing prior art. The other end of the pin-shaped member is in this case connected to a fitting. The shape of this fitting corresponds to the part of the body into which the pin has to be inserted, for example the part of the head of a pig behind the ear. Such a fitting is slightly curved.

It is important to place objects which are inserted with such injectors, such as transponders, in an accurately defined position. Preference is given to placing the transponders at an accurately defined distance and position behind the skin. Since the heads of, for example, pigs have a different curvature depending on the age and breed, it is necessary in the case of the device according to existing prior art injectors to use different fittings, otherwise it cannot be ensured that the transponder is positioned accurately in the desired place. Besides, it is possible with the fitting according to the existing prior art injectors to make a slight shift over the head part in question, so that the needle is inserted in slightly different positions relative to the adjacent skin, something which is undesirable. Costs and other inconveniences are also involved in the production and storage of different shapes of fittings.

SUMMARY OF THE INVENTION

The object of the present invention is to avoid these disadvantages. penetration of cut-off hair into the opening in the body of the animal, when a needle with bevelled end is used the tip thereof is preferably lying as close as possible to the pin-shaped member or is as far removed from it as possible. This latter design also has the advantage that engagement of the needle with the head can be made optimum. This effectively prevents the needle and the pin-shaped member from moving towards each other.

According to an advantageous embodiment of the invention, the pin-shaped member is provided so as to be movable essentially in the lengthwise direction relative to the injector. This is preferably achieved by pretensioning means, which drive the pin-shaped member outwards relative to the injector. When the pin-shaped member is in the correct position relative to the living being into which the object is to be inserted, during insertion of the hollow needle —which is also accompanied by a movement of the injector —the pin-shaped member will then essentially not move and will remain in a fixed position in the living being.

In order to be able to remove the needle easily from the animal and to ensure that the object to be inserted does not move out with it, the means for conveying the pin-shaped member through the needle are coupled to the pin-shaped member, i.e. the means for conveying through the needle, as it were, press the hollow needle out of the living being after the object to be placed is inserted at the correct position. This means that such a coupling does not take place until the moment at which the object is essentially in place in the body. During the return movement of the needle the pin-shaped member remains in a fixed position relative to the living being. Holding the pin-shaped member in a fixed position relative to the living being at different stages of the insertion and removal of the hollow needle ensures that no friction or other hindrance occurs through puckering of the skin and the like, so that operation of the injector is made easier. In all these embodiments it is possible for a blade to be placed on the free end of the pin-shaped member, which blade is designed to lie flat against the body of the living being. Such a blade must distinguished from the fitting according to existing prior art injectors, because such a blade fixes only the direction of rotation of the injector relative to the living being, while the other position of the injector relative to the living being is determined by the shank part of the pin-shaped member and the stop means, if present.

BRIEF DESCRIPTION OF THE DRAWINGS

The invention will be explained in greater detail below with reference to an example of an embodiment shown in the drawing, in which.

DETAILED DESCRIPTION OF THE PREFERRED EMBODIMENTS

Figure 1:
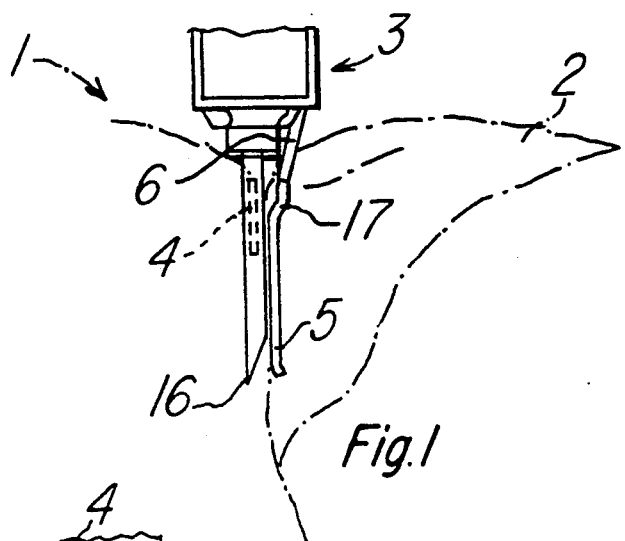
FIG. 1 shows schematically in rear view a living being with an injector according to the invention placed in the insertion position.

FIG. 1 schematically shows a rear view of a pig's head and the injector's orientation with respect to the pig's head. The head has an ear 2. The injector 3 according to the invention, only partially shown, is placed in the space formed where the ear is joined to the head. With such an injector 3, objects such as transponders 4 are placed under the skin of an animal. Such transponders can be used, inter alia, for registration purposes.

Figure 2:
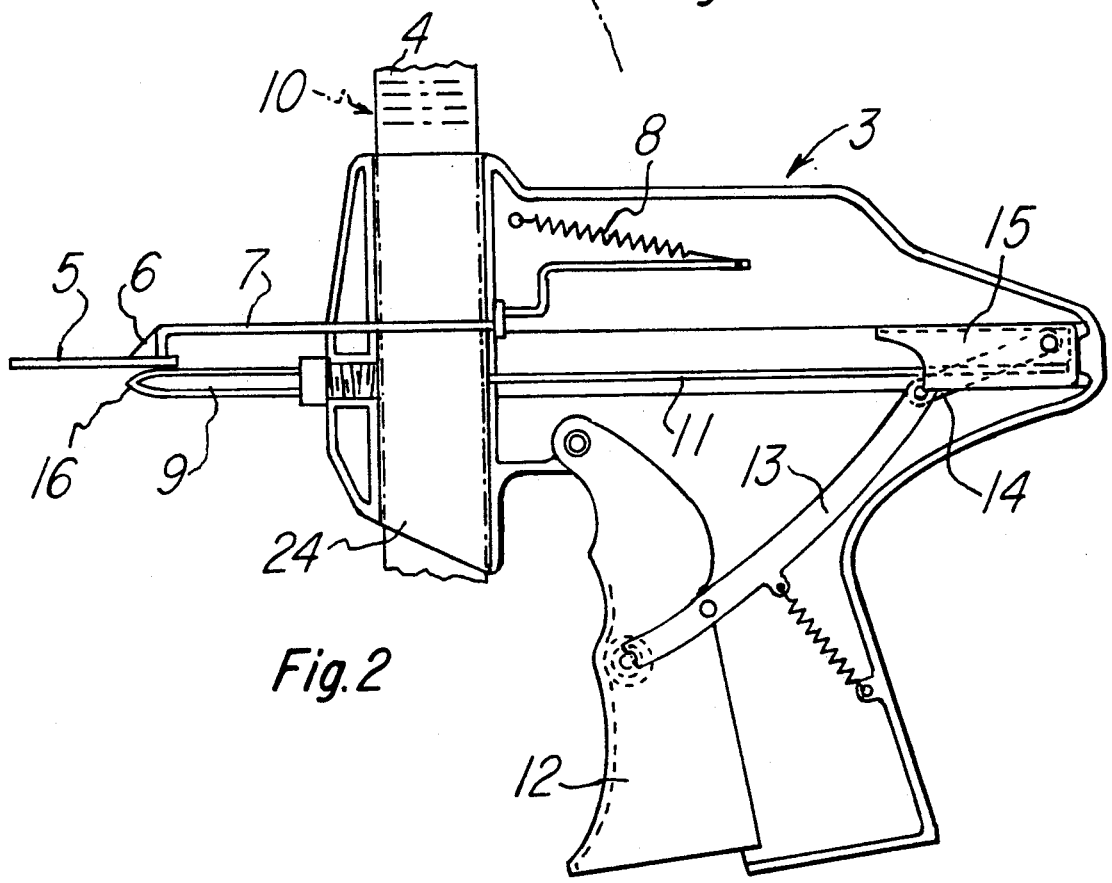
FIG. 2 shows the injector according to the invention in the released position.

FIG. 2 shows the injector according to the invention in its entirety. It can be seen that it comprises a pin 5 bounded at one end by a stop 6, which stop is in turn connected by means of a spacer 7 to the injector housing 24. Spacer 7 is made slidable relative to the injector housing 24 and is driven to the outside position by means of spring 8.

A hollow needle 9 is also present for the accommodation of transponders 4. Said transponders 4 are accommodated in a cartridge 10, which is moved by any kind of generally known means through the injector housing 24. The transponders 4 are driven by means of a push rod 11 out of the cartridge 10 into the hollow needle 9 to the position for placing in the living being. It is, of course, possible to place the transponders 4 in the hollow needle 9 in another way. The only essential factor is that push rod 11 should place transponders 4 in the correct position in the living being. Push rod 11 is operated by means of grip 12 and levers 13 and 14. Squeezing grip 12 causes push rod 11 to move to the left in FIG. 2. Lever 14 is also connected to a pressure block 15.

Figure 3:
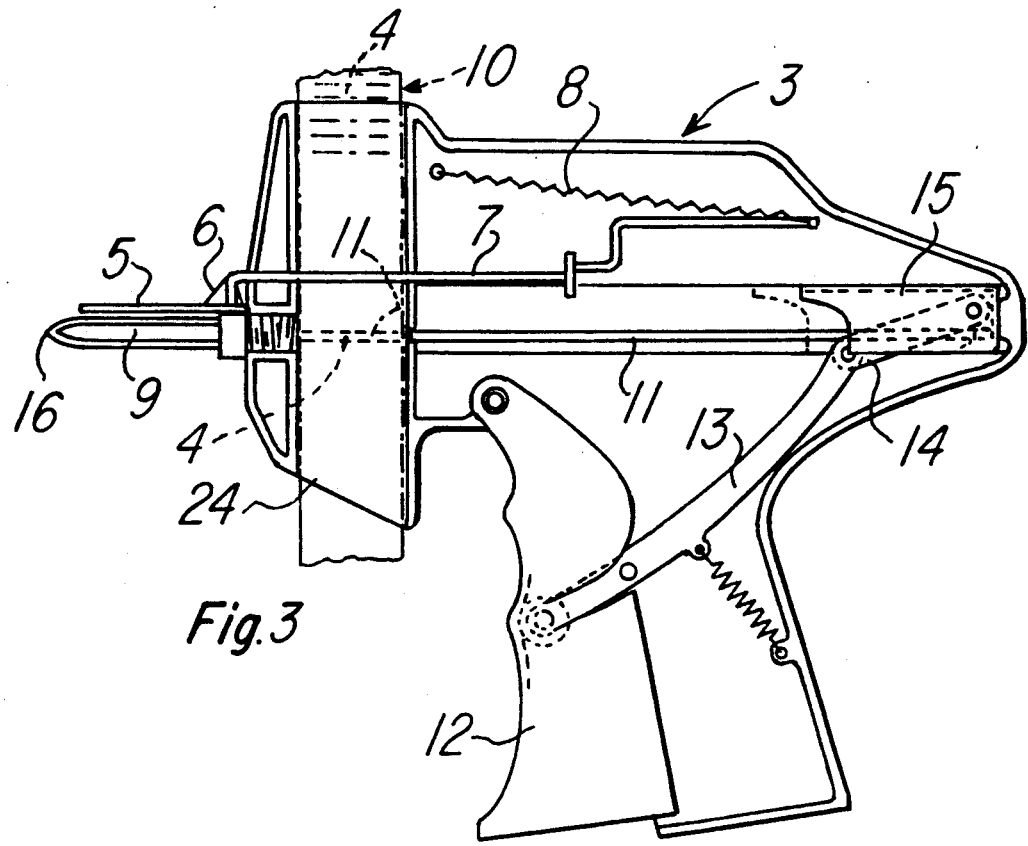
FIG. 3 shows the injector according to FIG. 2 in the position shown in FIG. 1.

FIG. 3 shows the position of the injector when it is being introduced into the living being, as shown in FIG. 1. Starting from the FIG. 1 position, in which stop 6 is placed against the connecting part between the head and the ear and pin 5 abuts against the part of the head near the ear, needle 9 is pressed inwards. This pressing inwards is produced by exerting a force on the injector housing 24. Since tip 16 of the needle is remote from pin 5, a good grip of the tip on the head of the animal is achieved, without any risk of slipping off. Such a placing of the needle also ensures that fewer hairs are cut off a pig than would occur with placing in another position. The amount of contamination introduced into the opening for the object is further limited in this way. When the needle 9 moves in the head of the animal, injector housing 24 moves along with it, but pin 5 with stop 6 remain in the same position against the animal, due to the fact that spacer 7 is displaceable relative to the injector housing 24. In order to prevent skin folds, which can occur during the insertion of the needle, from pressing pin 5 away, pin 5 is provided with a recessed part 17.

Figure 4:
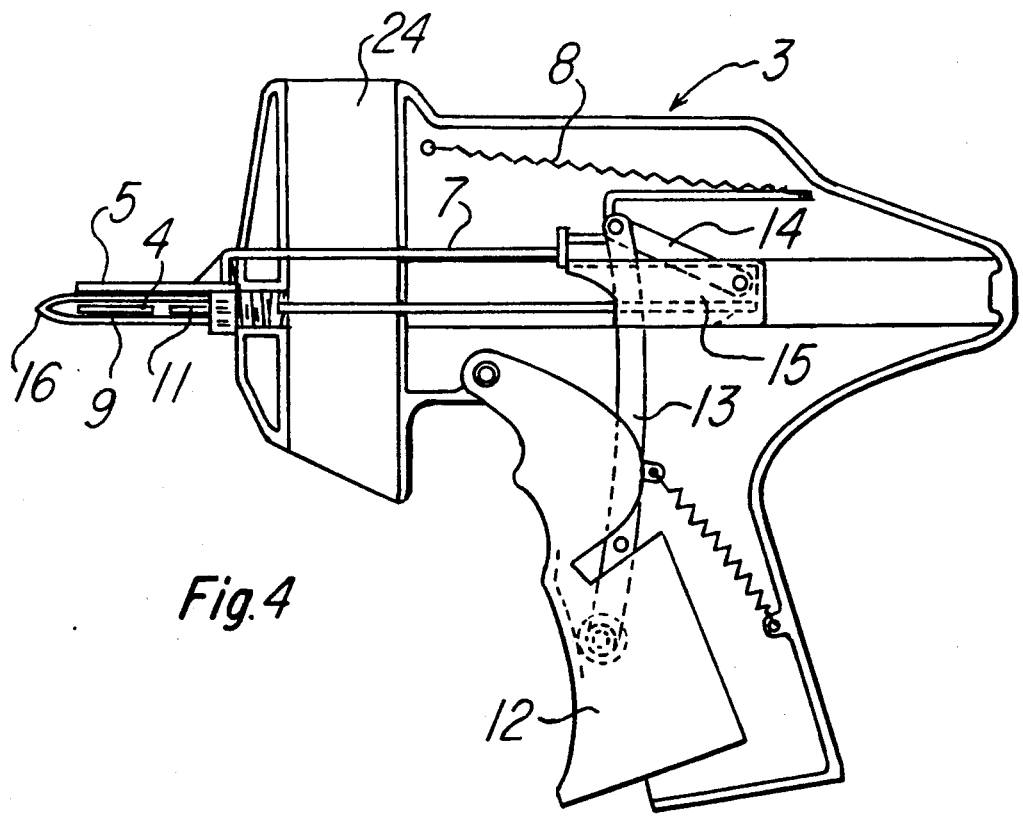
FIG. 4 shows the position of the injector during displacement of the transponder.

FIG. 4 shows the position when the first part of the movement path of grip 12 has been completed. It can be seen clearly that pin 11 has moved the transponder 4 out of the cartridge into the hollow needle. As in FIG. 3, pin 5 is still in contact with the space between the head and the point where the ear joins the head.

Figure 5:
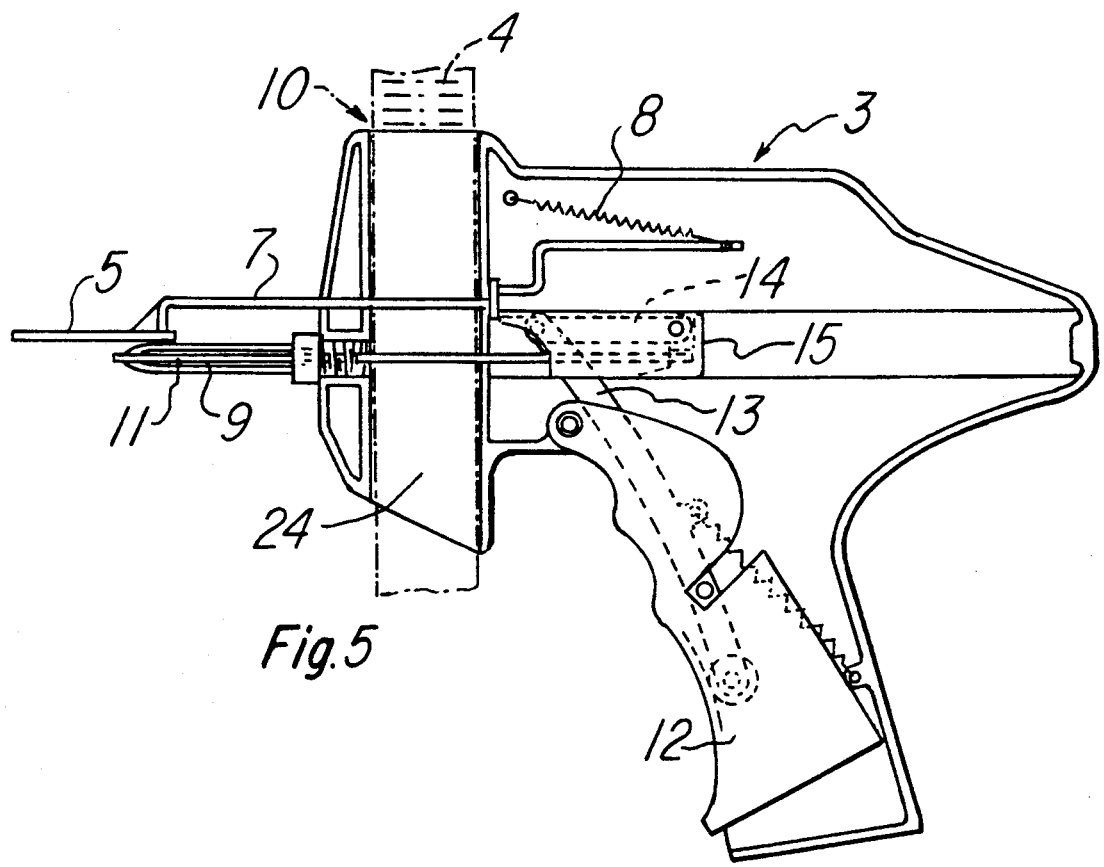
FIG. 5 shows the injector at the end of the outward movement of the hollow needle.

On further movement of grip 12, pressure block 14, as shown in FIG. 5, will act upon spacer 7, and the movement of push rod 11 and spacer 7 and thus pin 5 will be directed synchronously outwards. This results in injector 3 being moved outwards relative to the head of the living being and needle 9 being drawn back, while pin 5 remains in place. The outward movement of push rod 11 ensures that transponder 4 no longer moves back, but is held in the correct position under the skin of the animal. It is possible if desired to fit a blade or vane at the free end of pin 5, in order to limit rotation of injector 3 relative to the living being. Such a rotation is also largely limited by the stop 6.

Although the invention is described above with reference to a preferred embodiment, it must be understood that numerous modifications can be made thereto without going beyond the scope of the present application. It is essential for the position of the injector relative to the living being to be determined by the lateral resting of the pin against the head of the animal, and not by any fitting resting flat on the skin. The injector can be designed in all manners known in the state of the art.

We claim:

1. An injector comprising:
   a body having a front end and a back end;
   a grip extending downward from said body;
   a needle which protrudes from said front end of said body and provides a vehicle for the transport of objects;
   a means for conveying and placing objects via the needle in a mass, located within said grip and body of said injector; and
   positioning means, protruding from the front end of said body, for fixing the position of the needle relative to said mass, said positioning means comprising;
   a retractable pin-shaped member, fitted substantially parallel to the needle and having a connected end, connected to said front end of said body, and a free end characterized in that at the moment of insertion of the needle into the mass, the free end extends substantially beyond the end of the needle and retracts into the body of the injector upon inserting the needle further, and that a shank part of the pin-shaped member is adapted near the free end of said pin-shaped member to rest against the mass.

2. Injector according to claim 1, wherein the pin-shaped member further comprises a stop means located in between said connected end and said free end for limiting the amount said pin-shaped member retracts into said body of said injector.

3. Injector according to claim 2, wherein said pin-shaped member further comprises spacer means located between the stop means and said connected end of said pin-shaped member.

4. Injector according to claim 2, wherein the pin-shaped member is provided near the stop means with an offset bend in the pin-shaped member shank increasing the space between the parallel pin and needle.

5. Injector according to claim 1, wherein the end of the needle is bevelled and the tip of the needle is disposed towards the pin-shaped member.

6. Injector according to claim 1, wherein the end of the needle is bevelled and the tip of the needle is disposed away from the pin-shaped member.

7. Injector according to claim 1, wherein a blade is provided on the free end of said pin-shaped member, designed to lie against the body.

8. Injector according to claim 1, wherein the pin-shaped member is fitted so that it is movable essentially in the lengthwise direction relative to the body of the injector.

9. Injector according to claim 8, wherein the pin-shaped member is provided with pre-tensioning means which drive the pin-shaped member outward from the body of the injector.

10. Injector according to claim 1, wherein the means for conveying through the needle are coupled to the pinshaped member via pre-tensioning means.

11. Injector according to claim 10, wherein said coupling is achieved in such a way that from the moment that the object is essentially in place in the body, the movement of the means for conveying through the needle and the pre-tensioning means is synchronized.

12. Injector according to claim 1, wherein said pin-shaped member retracts upon said free end meeting some resistance created by contours of said mass.

* * * * *